United States Patent
Bodick et al.

[11] Patent Number: 6,090,829
[45] Date of Patent: Jul. 18, 2000

[54] METHOD FOR TREATING EXCESSIVE AGGRESSION

[75] Inventors: Neil C Bodick, Indianapolis; Franklin P Bymaster, Brownsburg; Harlan E Shannon, Carmel, all of Ind.

[73] Assignee: Eli Lilly and Company, Indianapolis, Ind.

[21] Appl. No.: 09/202,518

[22] PCT Filed: Jul. 28, 1997

[86] PCT No.: PCT/US97/13180

§ 371 Date: Dec. 16, 1998

§ 102(e) Date: Dec. 16, 1998

[87] PCT Pub. No.: WO98/05207

PCT Pub. Date: Feb. 12, 1998

Related U.S. Application Data

[60] Provisional application No. 60/022,914, Aug. 1, 1996.

[51] Int. Cl.[7] .................. A61K 31/4406; A61K 31/4436; A61K 31/4439
[52] U.S. Cl. ............................................. 514/342
[58] Field of Search ................................... 514/342

[56] References Cited

U.S. PATENT DOCUMENTS

| | | |
|---|---|---|
| 5,041,455 | 8/1991 | Sauerberg et al. . |
| 5,043,345 | 8/1991 | Sauerberg et al. ................ 514/342 |
| 5,328,923 | 7/1994 | Sauerberg et al. ................ 514/340 |
| 5,328,924 | 7/1994 | Sauerberg et al. ................ 514/340 |
| 5,488,056 | 1/1996 | Bodick et al. ................ 514/305 |
| 5,708,014 | 1/1998 | Bodick et al. ................ 514/340 |

FOREIGN PATENT DOCUMENTS

| | | |
|---|---|---|
| 0 307 142 A1 | 3/1989 | European Pat. Off. . |
| 0 384 288 A2 | 8/1990 | European Pat. Off. . |
| 0 709 094 A2 | 5/1996 | European Pat. Off. . |
| 0 723 781 A2 | 7/1996 | European Pat. Off. . |
| WO 94/20495 | 9/1994 | WIPO . |
| WO 94/29303 | 12/1994 | WIPO . |
| WO 95/05174 | 2/1995 | WIPO . |
| WO 95/17185 | 6/1995 | WIPO . |
| WO 96/13168 | 5/1996 | WIPO . |

OTHER PUBLICATIONS

Rapaport, et al., *Biol. Psychiatry*, 29, 658–664 (1991).
Katzung, B.G., *Basic & Clinical Pharmacology*, (Appleton & Lange, Norwald), 90–94 (1995).
Sauerberg, et al., *J. Med. Chem.*, 35, 2274–2283 (1992).

*Primary Examiner*—Phyllis G. Spivack
*Attorney, Agent, or Firm*—David M. Stemerick; MaCharri Vorndran-Jones

[57] ABSTRACT

The present invention provides a method of treating conduct disorder in a human using a compound of formula (I)

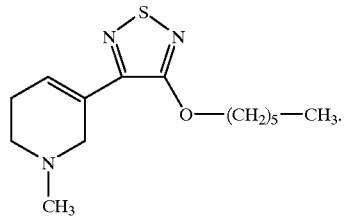

(I)

10 Claims, No Drawings

METHOD FOR TREATING EXCESSIVE AGGRESSION

This application claims benefit to U.S. Provisional 60/022,914 filed Aug. 1, 1996.

This invention provides a method for using 3-(4-hexyloxy-1,2,5-thiadiazol-3-yl)-1,2,5,6-tetrahydro-1-methylpyridine, (hereinafter referred as "xanomeline"), for the treatment of excessive aggression.

Excessive agression can be a problem for institutionalized patients and may be associated with violent suicides. Extreme aggressiveness can be harmful to the individual prone to extreme aggressivenes, may be detrimental to relationships and family members interacting with the individual, and may complicate the management of patients or prisoners in the institutional setting.

Studies of animals and human beings suggest that 5-HT serves a critical role in aggression and impulsivity. Several human studies report a correlation between low cerebrospinal fluid 5-HIAA and violent suicides. Therefore, extreme aggression appears to be associated with abnormalities in 5-HT. Goodman and Gillman, *The Pharmacololgical Basis of Therapeutics*, 257 (9th Ed. McGraw-Hill, New York, 1996).

However, there is a need for new treatments that can manage extreme aggression in a safe and ethical manner. Applicants have discovered that xanomeline can be useful for the treatment of extreme aggression. More specifically, the invention provides a method of treating extreme aggression in a mammal using 3-(4-hexyloxy-1,2,5-thiadiazol-3-yl)-1,2,5,6-tetrahydro-1-methylpyridine.

As noted hereinbefore, the compounds employed in the method of the present invention are known. Methods of preparing the compounds, as well as pharmaceutical formulations containing the compounds, are taught by Sauerberg in U.S. Pat. No. 5,043,345 (hereinafter refered to as the "'345 patent") herein incorporated by reference. The '345 patent teaches that xanomeline can be useful for treating Alzheimer's Disease and as stimulants of the cognitive function of the forebrain and hippocampus of mammals. Applicants have discovered that xanomeline can be useful for the treatment of extreme aggression. Xanomeline may address the long felt need for treatments which provide a favorable safety profile and effectively provides relief for the patient or individual suffering from extreme aggression.

The presently claimed invention provides a method for treating extreme aggression, comprising administering an effective amount of a compound of Formula I:

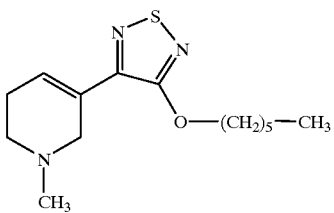

I or a pharmaceutically acceptable salt or solvate thereof to a patient in need of such treatment.

A preferred embodiment of the present invention is for use in the treatment of Conduct Disorder as characterized by the DSM-IV as catagory 312.8.

An especially preferred embodiment of the present invention is administering the effective amount transdermally using a patch.

The term "effective amount", as used herein, represents an amount of compound necessary to prevent or treat a mammal susceptible to or suffering from excessive aggression following administration to such mammal. The active compound is effective over a wide dosage range. For example, dosages per day will normally fall within the range of about 0.005 to about 500 mg/kg of body weight. In the treatment of adult humans, the range of about 0.05 to about 100 mg/kg, in single or divided doses, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way. While the present compound may be administered orally to humans susceptible to or suffering from extreme aggression, the compound is particularly well suited to be administered transdermally. When the compound is delivered transdermally, it is preferred that the effective amount is from about 10 mg to about 100 mg per day delivery of base compound. It is especially preferred that such patch delivers an effective amount for about one to seven days.

The compound may further be delivered by a variety of other pharmaceutically accepted routes including, but in no way limited to parenterally, subcutaneous, intranasal, intramuscular and intravenous routes. Such formulations may be designed to provide delayed or controlled release using formulation techniques which are known in the art.

Xanomeline may be administered as a feed additive when utilized for veterinary science purposes.

As used herein, the term "mammal" shall refer to the Mammalia class of higher vertebrates. The term "mammal" includes, but is not limited to, a human. The term "treating" as used herein includes prophylaxis of the named condition or amelioration or elimination of the condition once it has been established.

As used herein, the term "extreme aggression" shall refer to a condition characterized by aggression that is so extreme that it interferes with the individual's daily functions, relationships, and may threaten the safety of the individual, for example in a situation in which violent suicide is contemplated. The extreme aggression which may be treated using the method claimed herein shall be independent of a psychotic condition and not directly related to the consumption of a drug or other substance. The patient suffering from extreme aggression may, but is not required to, suffer from a Conduct Disorder, classified in DSM-IV-R as catagory 312.8. DSM-IV-R. *Diagnostic and Statistical Manual of Mental Disorders, Revised*, 4th Ed. (1994).

Xanomeline has been found to have a favorable profile of activity in a number of in vitro binding assays, designed to measure the degree of binding to neural receptors.

Xanomeline has been studied using accepted pharmacological methods such as oxotremorine-M verses N-methylscopolamine binding studies (Freedman et al. *Br. J. Pharmacology*, 93:437–445 (1988). Xanomeline inhibited the binding of $^3$H-oxotremorine-M with an inhibition constant ($K_i$) of 2 nM. The binding of the muscarinic ml antagonist ligand, $^3$H-pirenzepine, to ml receptors in hippocampus and $^3$H-quinuclidinyl benzilate to m2 receptors in brain stem was inhibited with $K_i$ values of 5 and 24 nM, respectively.

Muscarinic agonists stimulate the formation of cAMP up to 10 fold in CHO m4 cells treated with pertussisi toxin and the pharmacology is consistent with the mediation by m4 receptors. Eckols K. *Soc. Neurosci Abstr.,* 21:2040 (1995). In this assay, xanomeline efficaciously and potently stimulated the formation of cAMP. Such studies suggest that xanomeline predominantly activates m1 and m4 receptors. Further, accepted pharmacological studies have shown that xanomeline is active at the D2 receptor subtype.

The compounds employed in the invention are not believed to act via the GABA/benzodiazepine, 5HT1A, or D1 receptor systems in humans. Rather, the activity of the present compound as a treatment for excessive aggression is believed to be based upon modulation of muscarinic cholinergic receptors. However, the mechanism by which the present compounds function is not necessarily the mechanism stated supra., and the present invention is not limited by any mode of operation.

EXAMPLE 1

Human Clinical Trials

The activity of xanomeline for treating or alleviating excessive aggression can be demonstrated by human clinical trials. The study was designed as a double-blind, parallel, placebo-controlled multicenter trial. The subjects were randomized into four groups, placebo and 25, 50, and 75 mg tid of test compound. The dosages were administered orally with food. Subjects were observed at four visits to provide baseline measurements. Visits 5–33 served as the treatment phase for the study.

During the visits, subjects are observed for signs of aggitation, outbursts, mood swings, tremor, social withdrawal, and concentration abilities.

Treatment groups are compared with respect to the number and percent of subjects who ever had the symptom during the double-blind portion of the study (visits 5 through 33), at a severity that was worse than during the baseline visits (1 through 4).

What is claimed is:

1. A method for treating conduct disorder comprising administering to a mammal in need of such treatment, an effective amount of a compound of Formula I:

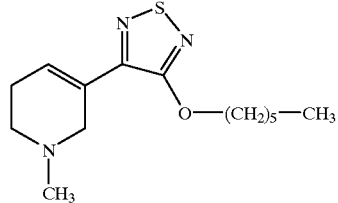

Formula I or a pharmaceutically acceptable salt thereof.

2. A method of claim 1 wherein the effective amount is from 1 mg/kg to about 100 mg/kg per day.

3. A method of claim 2 wherein the effective amount is from about 10 mg/kg to about 100 mg/kg per day.

4. A method of claim 1 wherein the effective amount is delivered using a transdermal patch.

5. A method of claim 4 wherein the transdermal patch delivers from about 10 to about 100 mg of base compound per day.

6. A method of claim 5 wherein the transdermal patch delivers an effective amount for one (1) to seven (7) days.

7. A method of claim 1 wherein the conduct disorder is severe.

8. A method of claim 7 wherein the effective amount is delivered transdermally using a patch.

9. A method of claim 1 wherein the conduct disorder is moderate.

10. A method of claim 1 wherein the conduct disorder is mild.

* * * * *